(12) United States Patent
Prince

(10) Patent No.: US 10,028,641 B1
(45) Date of Patent: Jul. 24, 2018

(54) COMBINED EAR, NOSE AND THROAT INSPECTION AND OPERATION INSTRUMENTS

(76) Inventor: John H. Prince, Los Altos, CA (US)

(*) Notice: Subject to any disclaimer, the term of this patent is extended or adjusted under 35 U.S.C. 154(b) by 1447 days.

(21) Appl. No.: 13/506,838

(22) Filed: May 18, 2012

(51) Int. Cl.
*A61B 1/018* (2006.01)
*A61B 1/04* (2006.01)
*A61B 1/06* (2006.01)
*A61B 1/00* (2006.01)
*A61B 1/07* (2006.01)

(52) U.S. Cl.
CPC ...... *A61B 1/00087* (2013.01); *A61B 1/00167* (2013.01); *A61B 1/00193* (2013.01); *A61B 1/00096* (2013.01); *A61B 1/00133* (2013.01); *A61B 1/00181* (2013.01); *A61B 1/0607* (2013.01); *A61B 1/07* (2013.01)

(58) Field of Classification Search
CPC ..... A61B 1/0607; A61B 1/07; A61B 1/00087; A61B 1/00096; A61B 1/00133; A61B 1/00167; A61B 1/00181; A61B 1/00193
See application file for complete search history.

(56) References Cited

U.S. PATENT DOCUMENTS

| | | | | |
|---|---|---|---|---|
| 3,605,725 A * | 9/1971 | Bentov | ............. | A61B 1/0052 600/434 |
| 4,217,891 A * | 8/1980 | Carson | ............. | A61B 1/00165 600/138 |
| 4,483,562 A * | 11/1984 | Schoolman | ............. | A61B 17/29 294/104 |
| 4,499,899 A * | 2/1985 | Lyons, III | ...... | A61B 17/320016 606/170 |
| 4,590,936 A * | 5/1986 | Straub | .................... | B26B 27/00 606/111 |
| 4,770,174 A * | 9/1988 | Luckman | ....... | A61B 17/320016 606/180 |
| 4,862,873 A * | 9/1989 | Yajima | ............... | A61B 1/00193 348/45 |
| 5,112,299 A * | 5/1992 | Pascaloff | ......... | A61B 17/32002 604/22 |
| 5,919,128 A * | 7/1999 | Fitch | .................. | A61B 1/00165 600/111 |
| 5,928,137 A * | 7/1999 | Green | ................ | A61B 1/00052 600/104 |
| 6,458,076 B1 * | 10/2002 | Pruitt | ................... | A61B 1/0051 600/128 |

(Continued)

*Primary Examiner* — John P. Leubecker
(74) *Attorney, Agent, or Firm* — James Ray and Assoc. IP LLC; Alexander Pokot

(57) ABSTRACT

An instrument for visual examination of and operation on internal body organs includes a jacket defining an operating end and a longitudinally opposite control end, an outer tube disposed stationary inside the jacket, and an inner tube disposed for a rotation inside the outer tube. A first blade is rigidly connected to the outer tube at the operating end while a second blade is rigidly connected to the inner tube, adjacent the first blade. First fiber optic bundles with polished ends are disposed within a wall thickness of the jacket and diffusers are attached to the polished ends at the control end. Second fiber optic bundles are disposed within the wall thickness of the jacket, interspersed with the first fiber optic bundles. Lenses are attached to selective first fiber optic bundle at the control end. A mechanism is positioned at the control end and coupled to the first and second blades.

19 Claims, 5 Drawing Sheets

(56) References Cited

U.S. PATENT DOCUMENTS

| | | | | |
|---|---|---|---|---|
| 6,547,720 B1* | 4/2003 | Street | A61B 1/00193 | 348/51 |
| 7,033,357 B2* | 4/2006 | Baxter | A61B 17/320016 | 606/41 |
| 7,599,588 B2* | 10/2009 | Eberle | A61B 1/00165 | 385/15 |
| 7,922,654 B2* | 4/2011 | Boutillette | A61B 1/00071 | 600/129 |
| 8,287,449 B2* | 10/2012 | Tanaka | A61B 1/0052 | 600/118 |
| 8,512,229 B2* | 8/2013 | Saadat | A61B 1/0008 | 600/106 |
| 8,562,516 B2* | 10/2013 | Saadat | A61B 1/0008 | 600/106 |
| 8,608,649 B2* | 12/2013 | McWeeney | A61B 1/00071 | 600/146 |
| 8,876,704 B2* | 11/2014 | Golden | A61M 25/0043 | 600/114 |
| 8,911,357 B2* | 12/2014 | Omori | A61B 1/00009 | 356/479 |
| 8,986,196 B2* | 3/2015 | Larkin | A61B 1/00087 | 600/104 |
| 2002/0120181 A1* | 8/2002 | Irion | A61B 1/07 | 600/178 |
| 2003/0133191 A1* | 7/2003 | Morita | G02B 27/225 | 359/464 |
| 2003/0163030 A1* | 8/2003 | Arriaga | A61B 1/00165 | 600/182 |
| 2003/0205562 A1* | 11/2003 | Vergeest | B23K 26/0648 | 219/121.72 |
| 2004/0263614 A1* | 12/2004 | Banju | H04N 13/0459 | 348/58 |
| 2005/0030621 A1* | 2/2005 | Takahashi | G02B 27/2214 | 359/464 |
| 2005/0203341 A1* | 9/2005 | Welker | A61B 1/012 | 600/130 |
| 2005/0286126 A1* | 12/2005 | Huang | G02B 27/225 | 359/465 |
| 2006/0041192 A1* | 2/2006 | Klootz | A61B 1/0607 | 600/178 |
| 2006/0170869 A1* | 8/2006 | Shestak | G02B 27/2214 | 352/57 |
| 2007/0036498 A1* | 2/2007 | Cianciotto | G02B 6/2817 | 385/115 |
| 2008/0064925 A1* | 3/2008 | Gill | A61B 1/00059 | 600/109 |
| 2008/0147018 A1* | 6/2008 | Squilla | A61B 1/00193 | 604/264 |
| 2009/0190096 A1* | 7/2009 | Chen | G02B 27/2214 | 353/7 |
| 2010/0198009 A1* | 8/2010 | Farr | A61B 1/00103 | 600/109 |
| 2012/0127570 A1* | 5/2012 | Sakai | G02B 27/2214 | 359/463 |
| 2012/0215065 A1* | 8/2012 | Mukherjee | A61B 1/00193 | 600/108 |
| 2012/0327199 A1* | 12/2012 | Chen | G02B 27/2214 | 348/51 |
| 2015/0272698 A1* | 10/2015 | Rolfes | A61B 19/5244 | 600/424 |
| 2016/0015245 A1* | 1/2016 | Iwasaka | A61B 17/3421 | 600/106 |

* cited by examiner

OPERATING END

COMBINED EAR, NOSE AND THROAT INSPECTION AND OPERATION INSTRUMENTS

BACKGROUND OF THE INVENTION

Field of the Invention

This invention relates to the visual examination of, and operation on, internal organs of the body through natural apertures such as the ear, nose and throat. By circumferentially enveloping the operating instruments such as forceps and scissors with a capacity to visualize in 3D, blind spots are minimized and a clear picture of the operating area is created. Out of necessity new instruments are created to work within this confining diameter, including tools for incision, ablation, fastening, evacuation and manipulation. For convenience to the surgeon images are taken in real-time and are shown on a circular glasses-free 3D screen nearby. Images can also be compressed in real time for compact storage, for high-speed transmission to remote 3D displays, or for analysis. The illuminating and sensing end of this invention is applicable in the visible and also throughout the electro-magnetic spectrum (including the infra-red and microwave portions), as well as to sonar and ultrasound. The mechanical end of this invention is applicable wherever remote cutting or manipulation is required through narrow, medium or broad apertures.

Description of the Related Art

An illustration of the related art as used for Ear, Nose and Throat (ENT) is shown in FIG. 1, in which a pair of scissors (or forceps) with long handles can be introduced, along with a fiber-optic illuminator-viewer ("endoscope") and an evacuation tube, into an aperture of a human body. These items are often introduced separately, with the illuminator on one side of the scissors or forceps, so that the far side cannot be well illuminated or visualized. In order for scissors to cut or forceps to clamp they have to be opened, possibly wider than the ear nose or throat passage. It is an awkward arrangement in which there is often little room to maneuver.

In the related art the endoscope is a flexible fiber-optic probe about 3-5 mm in diameter and 40 cm long, which must be viewed through an eyepiece affixed to the surgeons head and activated with the surgeons left hand while the operation progresses. The surgeon now holds in his right (or left) hand tools which he cannot otherwise see except by his spare eye or by removing his headpiece.

In ENT it would be of great benefit if the surgeon could see his work in real time and independently on a nearby screen—and in color—so that he can focus his instruments with both hands on the present operation. This is done rarely.

SUMMARY OF THE INVENTION

Because it is difficult to manipulate incisors or forceps (with their long handles) in confined spaces, we have introduced a design using circular scissors, in which the long handles are replaced by rotating coaxial tubes of an arbitrary length to transfer the cutting or clamping force from the surgeons hands to the operating area within a diameter of an outer tube. These tubes will normally be rigid but can also be (as will be shown) flexible Because some of the tools, such as scissors or forceps are (in the present invention) designed to rotate in order to function, and for ease of insertion into body apertures, the optimal aspect of the instrument is cylindrical.

Around the outer fixed tube of the scissors or forceps is added a sleeve containing optical fibers, some to convey light, and some to convey images, and with wires for manipulating the cutting end. The thickness of this sleeve may be little more than the diameter of a bundle of optical fibers and (in practice) of the order of one to one and a half millimeters.

Having the optical fibers outside the area of the operating elements means that the scene can be viewed from its maximal aspect in 3D, and (as will be described) in a manner to virtually eliminate blind spots.

Since the optical fibers can be arranged in any pattern on the periphery, any combination of opposing bundles can be used for the creation of 3D, not even necessarily on the diameter, depending on the surgeon's needs. If the surgeon wishes to see another 3D view orthogonal to the first he can simply switch to it. This will be described.

The optimal viewing of the area of area of interest is to combine any number of matched detectors to produce a circular image, which can then be projected onto a screen and through a Fresnel lens to produce true parallax 3D, to be viewed without glasses. In this embodiment the screen will be close to the surgeon and will not be large, since the Fresnel system requires a commensurate projection distance which would mitigate against using a larger screen. Since it is close by the surgeon can view the image from all angles, and even if necessary see around the image, revealing no blind spots.

The depth of field for 3D (using 1° convergence as an arbitrary metric) would be from 10 mm to 60 mm. At this depth of field the diameter of the viewing lenses (at 6 mm) may optimal for intimate work.

Manipulating threads or wires within the outer sleeve steer the operating head (to some degree) using a track-ball and a gimbal. This will be illustrated.

Included advantages of the tubular arrangement are that the central lumen can be used for evacuation of debris or for the introduction of other modalities, such as ablation tools.

The size (diameter, wall thickness and length) of the tubes depends on the function. The diameter can range from the order of a millimeter upwards.

In addition to the surgeon's physical manipulation the cutting tools can be mechanized using (for example) vibrating piezo crystals for activating incisors with multiple cutting edges

BRIEF DESCRIPTION OF THE DRAWINGS

This invention, together with further advantages to be noted, may best be understood by reference to the following descriptions taken together with the accompanying drawings, in the several figures of which like reference numerals identify like elements, and in which.

DETAILED DESCRIPTION OF THE INVENTION

Figure 1:
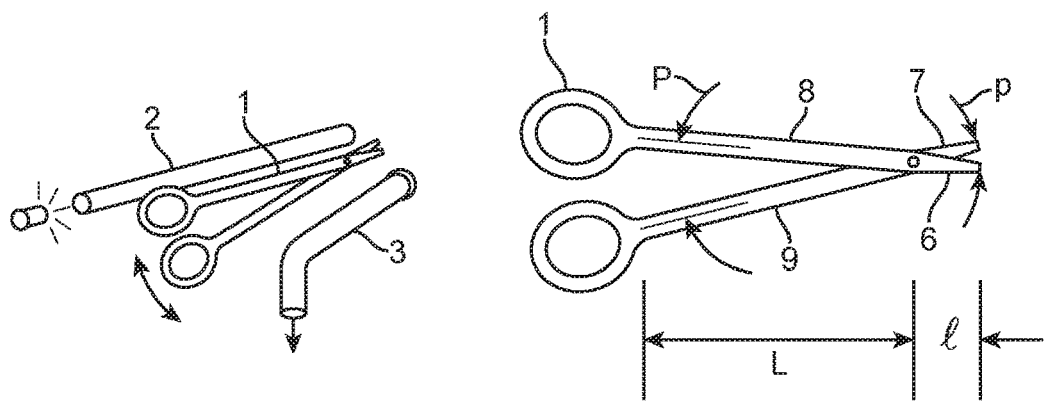
FIG. 1 shows the current state of the art, a pair of forceps or scissors 1 with a fiber-optic illuminator/sensor 2 placed alongside, with an evacuation tube 3 (for debris) nearby.

FIG. 1 shows prior art, a set of scissors 1 with wide-opening handles 8 and 9 opening to a width P and blades 6 and 7 opening to a width p. In the medical industry the length of the scissors L are generally of the order of 140 mm or 5.5". If the blades are required to open to 5 mm or ¼" for cutting then, with a mechanical advantage of 10:1, the handles must open to 50 mm or 2". This is prohibitively wide for narrow openings in the human body such as the nose.

Again in FIG. 1 the illuminating and viewing fiber 2 is typically inserted separately alongside the scissor handles. This will illuminate and view only one side of the operating area. It may not necessarily be well aligned, and will have a tendency to move during incision. This will create varying blind spots around the blades.

Also in FIG. 1 for evacuation of debris another tube 3 of about 5 mm diameter will need to be inserted in the area of the blades. This will take up more space.

The tools 1, 2, and 3 (and others) are sometimes introduced sequentially. This may not be as convenient as having them in place simultaneously.

Figure 2:
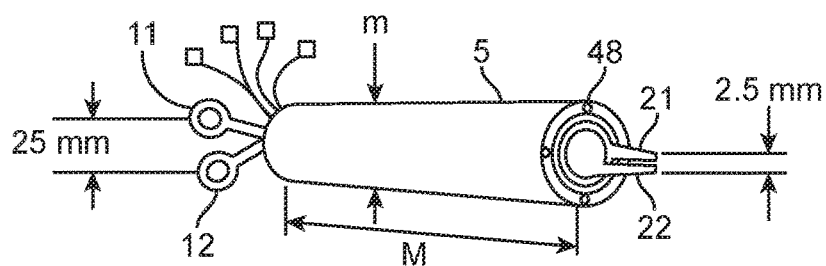
FIG. 2 shows a sketch of the present invention, a pair of rotary forceps or scissors surrounded with the fiber optic illuminators and sensors in a circular ring

FIG. 2, the subject of the present invention, may be directly compared against FIG. 1

FIG. 2 shows a fundamental reason for the present invention, the need to uniformly illuminate and visualize the area of an operation. FIG. 2 shows all the tools for a successful operation compacted into a diameter m and an arbitrary length M—the illuminating sources, the visualizing fibers, the manipulating wires, the scissors, and the evacuation or access tube.

Figure 4:
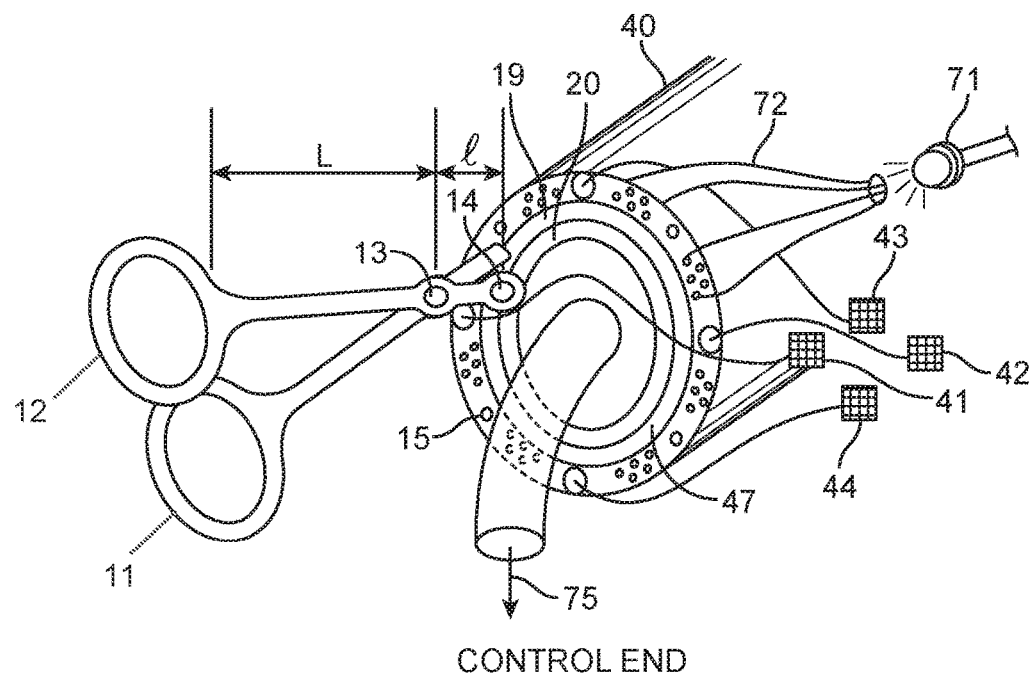
FIG. 4 is an illustration of the control end of the instrument, showing the scissor handles, with fiber-optic bundles going to detectors 41, 42, etc., illuminating fibers coming from an LED 71, and a flexible evacuation tube 75 emerging from the lumen.

In FIG. 2 shows an operating instrument 5 with the blades 21 and 22 opening to a width of 2.5 mm, and with a mechanical advantage of L/e or 10:1 (as shown in FIG. 4), the handles 11 and 12 will open to a width of 25 mm or 1". However this opening of the handles is now remote from the site of the operation by an arbitrary distance M of a tube which can be more than the length L (140 mm) of the scissor handles shown in FIG. 1. Importantly, the tube diameter m, as is the tube length M, is completely unaffected by the action of the scissors. Insertion of the circular scissors is now possible remotely and through narrow apertures in the human body such as the nose.

Figure 3:
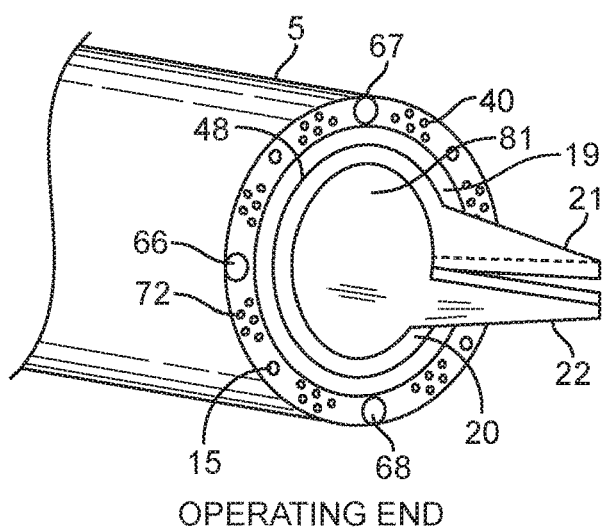
FIG. 3 is a blow-up of the working end, showing a scissor blades fixed to the inner and outer tubes, various illuminating fibers, and an arrangement of optical sensing fibers

FIG. 3 shows the working end 48 of the operating instrument 5 in detail.

In FIG. 3 the blades 21 and 22 are affixed to, or are integral to, concentric tubes 19 and 20. In this arrangement the outer tube 19 is fixed and the inner tube 20 is free to rotate, and is actuated by squeezing together the handles 11 and 12 remotely at the control end 47, resulting in the blades 21 and 22 crossing each other as scissors. Handle 11 has a connection with tube 19 and handle 12 has a connection 14 with the tube 20. Furthermore, handles 11 and 12 have a common connection 13. 81 is the lumen, an area inside the inner tube 20, which can be used for evacuation and for access with ablation or other tools.

Again in FIG. 3 the outer fixed tube 19 is surrounded by a jacket or tube 40 containing illuminating fibers 72, lenses 65, 66, 67 and 68 (see FIG. 8) and manipulating wires 15 at their tips. The illuminating fibers 72 are dispersed within the sheathing to give uniform illumination at the operating face 48. Their intensity is controlled by a dimmable light emitting diode 71 near the control end 47.

Figure 5:
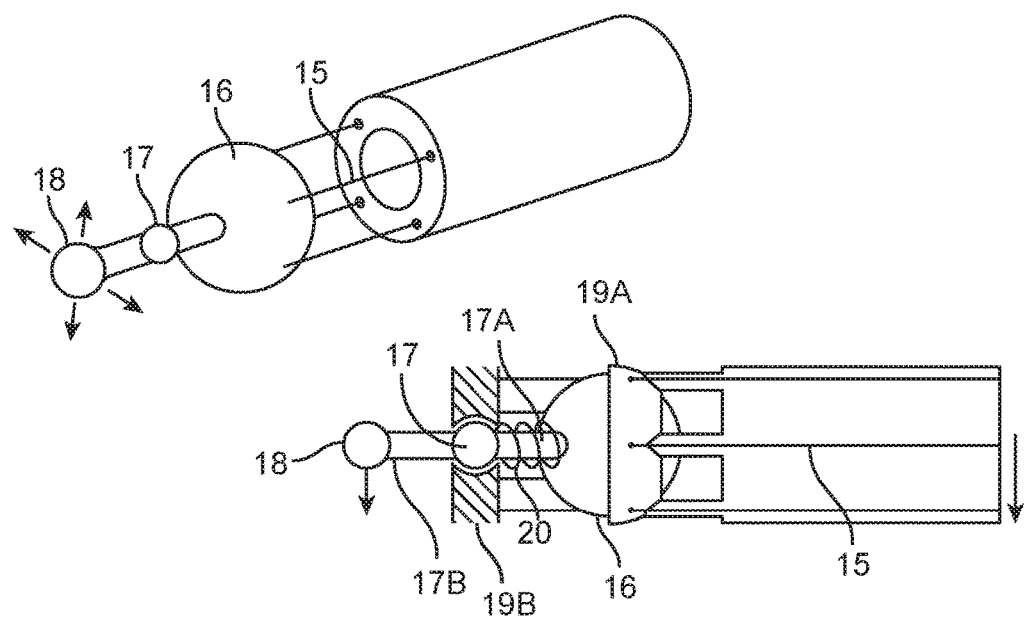
FIG. 5 shows a toggle arrangement for the manipulating wires 15 using as trackball 16, a pivot 17, and a knob 18.

FIG. 4 shows the control end of the instrument. The fiber-optic bundles from the optics 65, 66, etc. go to detector arrays 41, 42, etc. Up to the limits of the jacket there can be any number of fiber optic bundles with imaging lenses and detectors, as will be explained. How the fibers image on the sensors, how the sensor arrays are aligned, and how the images are manipulated will be described in detail below FIG. 5 shows a possible toggle arrangement for the manipulating wires 15, using a trackball 16 mounted for a rotation in a seat 19A and being attached to wires 15 passed through seat 19A, a pivot 17 that is disposed in the plate 19B and is connected to the trackball 16 with a first portion 17A, a spring 20 disposed about the first portion 17A and caged between a surface of the plate 19B and a surface of the trackball 16, and a knob 18 that is connected to the pivot 17 with a second portion 17B. When the knob 18 is pressed left the head is steered left. In this simple arrangement the steerage is limited mechanically by the stiffness of the tubes. However in one arrangement the head may be kept stiff, and the blades precisely coupled, while allowing the length to be to some degree flexible. Small sections of bellows or strong polymer may be used to transfer torque.

We may note that the scissor handles can be either left- or right-handed, as can the scissor blades. Properly situated the knob 18 can be manipulated by the thumb that holds the scissors.

Figure 6:
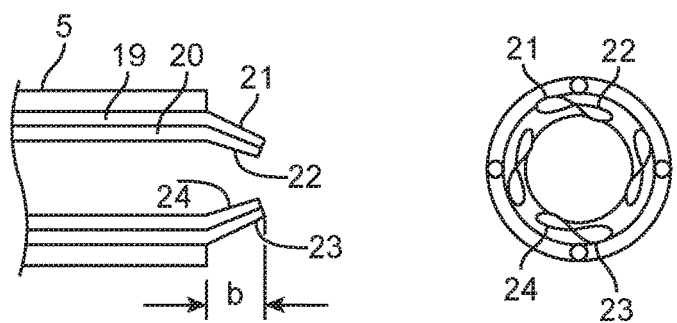
FIG. 6 shows cross-sections of the working end of the rotary scissors, with various blade arrangements, including angled blades.

FIG. 6 shows various arrangements of scissor blades. There can be more than one set blades, for example such as blades 23 and 24, symmetrically or otherwise arranged around the circumference. In one arrangement the blades will taper inwards, allowing illumination and excellent visualization of the area at their tips. The blades will have inner curvatures matching the distance of their cutting edges from the centerline. Blades 21 and 22 (and others) have cutting edges typical of scissors with the same inner curvatures as their associated tubes 19 and 20.

Figure 7:
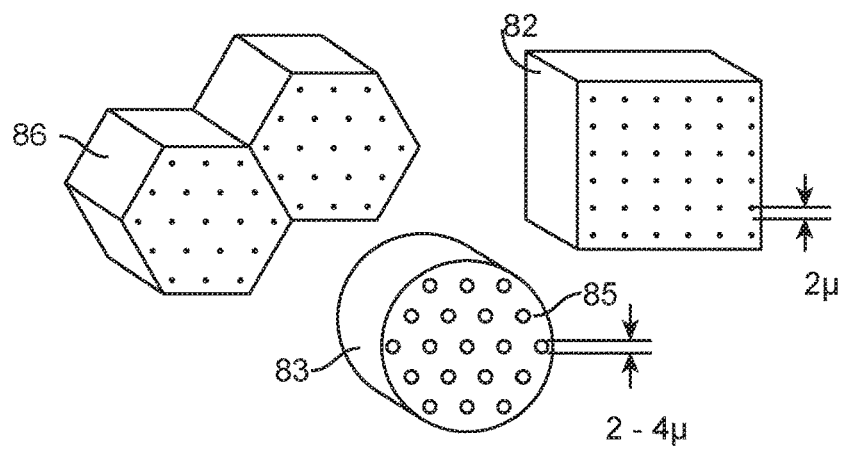
FIG. 7 shows various configurations of fiber optics for carrying the optical content from the imaging lenses to the detectors.

FIG. 7 shows several possible configurations of fibers. 86 shows two bundles of 19 2µ fibers. Together 10,500 such bundles will make up a coherent array 1 mm in diameter containing approximately 200,000 fibers. 82 shows a rectangular array of 400×500 fibers, also giving 200,000 fibers. 83 shows fiber with an aggregate of 19 holes 85, each 2µ in diameter. This creates a "holey" fiber 10µ in diameter, which when combined 10,500 times gives 200,000 holes.

Once again in FIG. 7 other aggregations, such as 37, 61, 91 or more holes on a hexagonal arrangement, are possible. The diameter of these holes (for the infra-red) is often 4µ, but for visible light which is of shorter wavelength (as in this case) 2µ is more convenient, as will be shown. Increasing aggregations of holes create stiffer array bundles, but also make coherent bundling easier. For example, an aggregate of 91 holes each requires only 2,100 fibers to create 200,000 holes.

The number 200,000, the hole diameter 2µ, and the diameter 1 mm are not arbitrary, but are modeled on the diameter of cones in the human eye (2µ), the diameter of the fovea centralis (1 mm), and the number of optic nerves (200,000). These optic nerves are responsible for the human eye's entire visual acuity, amounting to 50% of the eye's nervous output. (The balance of the eye's output, from the area containing 99% of the rods and cones, does not contribute to acute vision).

Analogous to optic nerves the function of individual fibers is not to carry images but to carry binary information. This information is carried as a combination of intensity (luma) and color. It can be sensed on a $Y'C_B C_R$ scale by each appropriate pixel on the detectors.

By no small coincidence the size of pixels on a typical CMOS chip is also 2µ. This means that lining up the ends of the fiber holes on a CMOS chip 45, as in FIG. 8, results in very fine imaging. A diffuser screen 55 placed between the polished fiber end 51 and the detector 45 works very similarly to invisible "scotch" tape, diffusing the light into the pixels, meaning that the hole pattern (hexagonal) does not need to line up precisely with the CMOS pixel pattern (rectangular) in order to produce good images. Finally, the matching of images between the various detectors 41, 42, etc. to produce good 3D requires various degrees of alignment, as will be described later FIG. 7 also shows a rectangular array containing 200,000 individual 2µ fibers. Taken together these have the advantage of being able to align closely on a CMOS chip with 2µ detectors. Since the fibers are relatively short (30 cm to 50 cm) they are coated with a thin (0.08µ to 0.1µ) metallic film to transport light without appreciably increasing thickness. As individual fibers they are fragile and hard to bundle coherently, but are very flexible.

Figure 8:
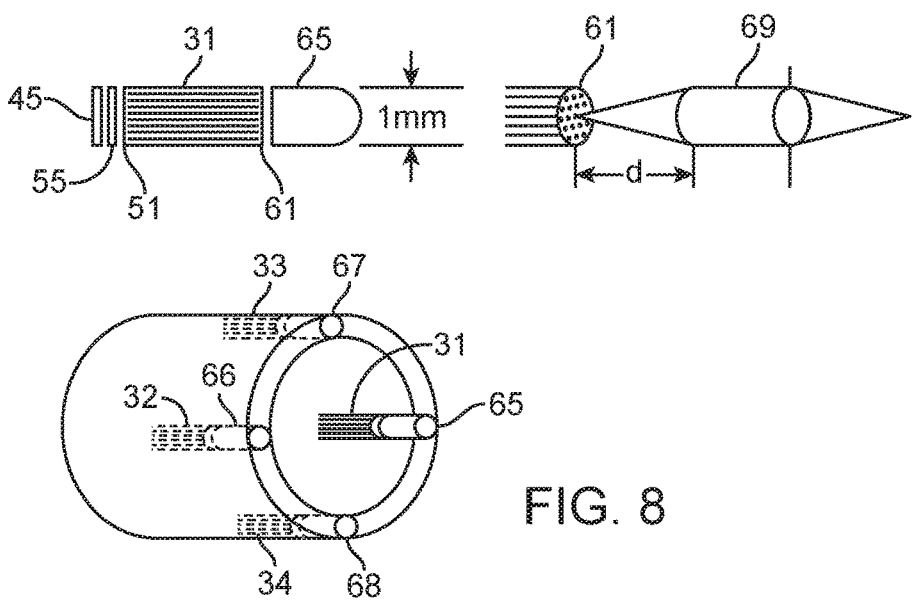
FIG. 8 shows various arrangements of fibers and optics for transporting images from the operating area to the detectors.

FIG. 8 shows two systems for imaging onto single bundles of fibers at the operating end of the instrument 48. The first is a rod lens 65 1 mm in diameter imaging onto a fiber bundle 31. This lens images organ tissue (at a mean distance of 1 cm) onto the back end of the lens, which is flat and in contact with the polished end 61 of the fiber. A second (alternate) lens 69 is a Selfoc lens also 1 mm in diameter, which images the organ tissue across a small gap d (depending on the lens's focal length) onto the same polished fiber end 61.

In FIG. 8 the imaging lenses 65, 66, etc. may in any number and in any arrangement 72 suitable for a corresponding 3D display, as will be described below.

Figure 9:
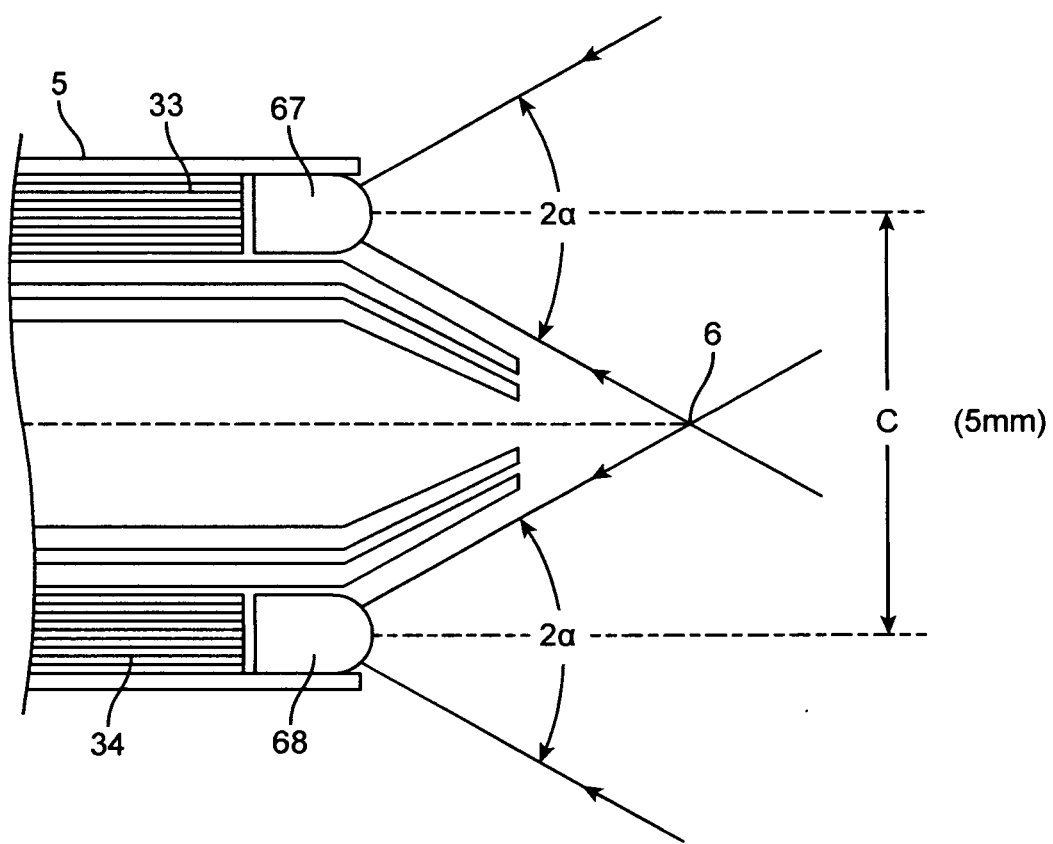
FIG. 9 shows the field of view of the imaging lenses as the fields converge towards the tips of the incisors

In FIG. 9 are shown two fiber bundles 33 and 34 together with their imaging lenses 67 and 68, appearing at the operating end of the subject instrument 5. The acceptance angle of the imaging lenses 2α is such that their fields of view overlap at a distance 6 of about 10 mm from the end. These overlapping fields enable the creation of 3D images where they are needed, near the tips of operating tools 21 and 22.

Again in FIG. 9, the acceptance angle 2a of the imaging lenses can in fact be much larger—as high as 120°—bringing the image overlap to within 2 mm of the face 48. The point of overlap 6 has now come very close to the face 48. Referring to the illustration in FIG. 3 this means that lenses 66, 67, and 68 can view the blades 21 and 22 cutting from one side in 3D while lens 65 (hidden in this figure) can see the tissue being cut from the other side. The surgeon will have a very clear picture of the operation from both sides.

Figure 10:
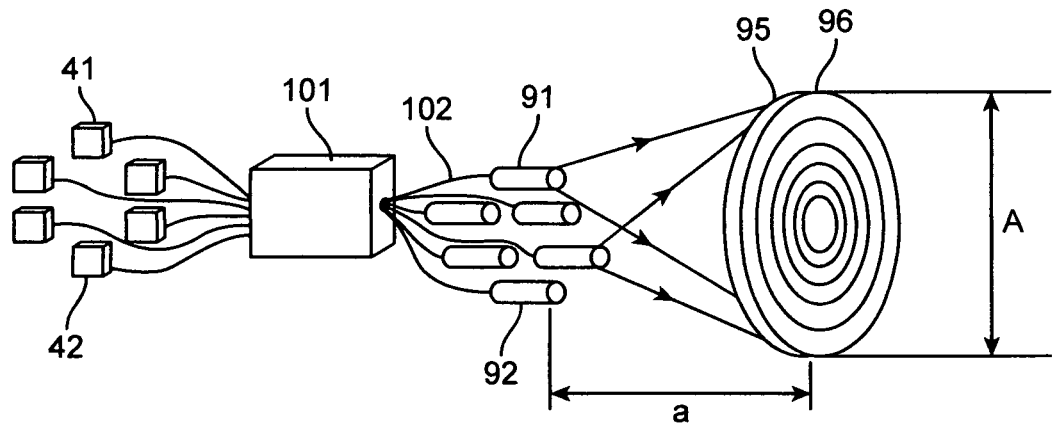
FIG. 10 shows the pathway from the detectors through a processor 101 to projectors 102 and to a display screen 95.

FIG. 10 shows an arrangement for a glasses-free 3D display. The outputs from the detectors 41, 42, etc. are fed into a display processor 101 which performs multiple functions (such as image rectification, inversion and amplification). The signals are fed into projectors 91, 92, etc. in a spatial arrangement 102 corresponding to the spatial arrangement of the input lenses 65, 66, etc. on the head 48 of the operating instrument 5.

In FIG. 10 the spatial arrangement 102 is magnified in size from the original imaging lens arrangement 72 commensurate with the size of the required display 96. In this case, being in close proximity to a surgeon, the diameter A of display screen has been chosen to be 50 cm. The requirement that the projected images overlap on a screen 95 determines the distance a to the projectors 102. A convenient distance a from the projectors 91, 92, etc to the screen 95 to match the screen size A is also approximately 50 cm.

In FIG. 10 in order to create 3D it is necessary that the translucent ("silver") screen 95 is adjacent to, if not actually touching, a Fresnel lens 96, which is where 3D is created. The Fresnel lens will have a focal length corresponding to the distance a of about 50 cm.

Figure 11:
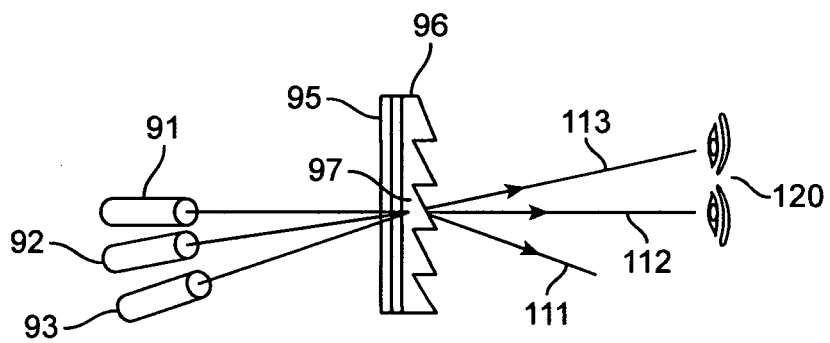
FIG. 11 shows how the Fresnel lens allows the creation of many images from multiple projectors to create 3D.

The Fresnel lens works as shown in FIG. 11. In this example three projectors are shown casting separate images onto the translucent screen 95, then through a prismatic section 97 of the Fresnel lens 96. These images are taken from slightly different viewpoints, so when an observer's left eye 120 is at point 111 the eye sees the images from projector 91, at point 112 the images from projector 92, and at point 113 the images from projector 93. The right eye sees corresponding offset images from adjacent projectors. These images are summed in the observer's mind over all the prismatic sections he can see at any moment in the Fresnel lens. In each case the perspective is appropriately different for each eye so the observer gets a sense of moving around the image. The function of the diffuser screen 95, in addition to providing a cinematic screen, is also to smooth the transition between adjacent images with minimal loss of resolution. With many well-coordinated projectors an observer will sense enough reality that he will see the images as stand-alone 3D objects. It will be noted that the positions of the projectors 102 are in fact inverted from the positions of the observing lenses on the instrument face 48.

A surgeon two or three feet from the screen, by moving his head slightly, can see above, below, and around the area of the operation. In other words, the surgeon will have a true panoramic 3D view of the entire operation, depending on the combined fields of view of all imaging lenses 65, 66, etc. at the tip of the operating instrument 5.

It may be seen that the alignment of the detectors and projectors is critical to the realization of good imaging. The alignment of the detectors is covered by other patent applications of the inventor. A synopsis is given here.

The stages of alignment of the detectors are rough, intermediate and fine. For these stages of alignment the processor 101 is connected temporarily to a keyboard 104 and a 2D screen 105 as in FIG. 11. The keyboard is for typing in commands and the 2D screen is for visualizing results. The screen will show multiple images from detectors 41, 42, etc. By referencing one of the images (such as image 141 from detector 41) and by a mechanical means (described elsewhere) the detectors 41, 42, etc. are rotated and translated with respect to the ends of the fibers 51, 52, etc. to bring the images into the best possible alignment on the screen. To avoid the confusion of multiple images this is done sequentially. In each case, the detectors are recording from different viewpoints so the images will not line up completely. However since the images may still be off by a few pixels this will require an intermediate stage of alignment.

Figure 12:
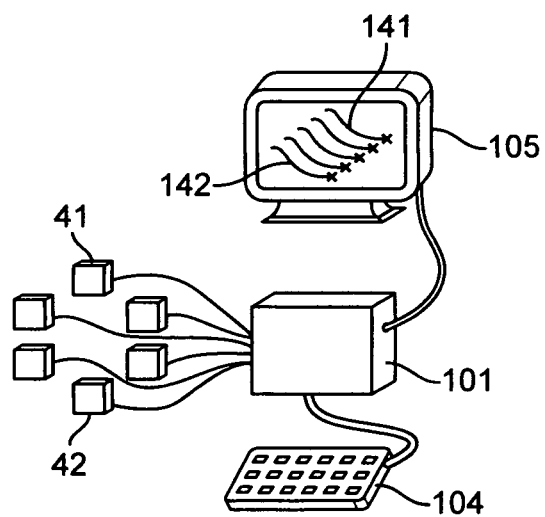
FIG. 12 shows a set-up to enable alignment of the detectors in order to produce quality 3D.

Referring to FIG. 12, the intermediate alignment is done in software through processor 101, where we have a choice of two (or more) approaches. One is to take the pixels of two entire frames, such as those from detectors 41 and 42, and using one frame as reference we bring the pixels from one detector into correspondence with the pixels from the other. This may be accomplished using a simple program, as in Matlab. That is, we reassign the pixels in detector 42 to conform to those in reference detector 41, and so on until the pixels in all detectors 43, 44, etc. have been reassigned. This is safe since the rough alignment has already brought the pixels of all detectors into close agreement, and few will fall out of bounds.

Another approach is feature based. We choose two recognizable (and well-separated) features as seen by all detectors 41, 42, etc. We choose one (41) as a reference and in a step-wise procedure compare all other features against it. For purposes of alignment the two features may be viewed together in each image as single threads 141, 142, etc. on the screen 105.

Using a notation common in imaging (See Richard Szeliski, December 2006), we may utilize the minimum of the sum of squares function $E_{SSD}(u)$ for our step-wise correlation of features 141, 142, etc.:

$$E_{SSD}(u)=\Sigma_i[I_1(xi+u)-I_0(xi)]^2=\Sigma_i(ei)^2$$

Where u=(u, v) is the feature displacement on orthogonal axes and $ei=I_1(xi+u)-I_0(xi)$ is the error function or feature displacement offset within the feature areas ($I_0$ being the reference feature image 141 and $I_1$ the subsequent sample 142, etc.

That is, we reduce all the errors ei to an acceptable minimum, realizing that because the images are taken from different perspectives, they will never be completely zero.

This approach has the advantage of correlating similar images within the confines of existing frames and towards the center, where convergence is more critical. It avoids the problem of outliers. It is also quicker.

For really fine correlation we use a partial differential equation to compare the image gradients at the light-to-dark edges of features 141 and 142. We now treat the least squares function $E_{SSD}(u)$ above as an energy function with a hypothetical displacement $\Delta u$ $$E_{SSD}(u+\Delta u)=\Sigma_i[I_1(xi+u+\Delta u)-I_0(xi)]^2=\Sigma_i[J_1(xi+u)\Delta u+(ei)]^2$$

where the Jacobian $J_1(xi+u)=\nabla I_1(xi+u)=(\partial I_1/\partial x, \partial I_1/\partial y)(xi+u)$ is the image gradient at (xi+u) and $ei=I_1(xi+u)-I_0(xi)$ is the intensity error (as above).

This is a soluble least squares problem in which sub-pixel resolution can be achieved when the Jacobians of the profiles of the two features 141 and 142 are approximately equal $$J_1(xi+u) \approx J_0(x)$$

since near the correct alignment the appearance of light-to-dark edges should be the same.

Assuming that the detectors 41, 42, etc. are looking at approximately the same aspect of the field, then what we have done (sequentially) with their images 141, 142 etc. has been to correlate them to within sub-pixels.

With these correlations the outputs from processor 101 will now flow coherently to projectors 91, 92, etc.

The same images 141, 142, etc. which appeared on screen 105 will now show up on screen 95 for viewing through the Fresnel lens 96. The same process of careful alignment must now be carried out on each of the projectors 91, 92, etc. so that the images overlap perfectly. This alignment will be mostly mechanical, with iterations between viewing the display and adjusting the projectors one by one until the best possible image appearances are achieved.

Having gone through these adjustments and alignments, because the pixel designations are prescribed, the images will appear on the screen in very nearly real-time.

In this arrangement the larger the number of projectors the smaller will be the intervals at which the images will shift from one perspective to another, and consequently the smaller and smoother the transitions. The number of detectors to match the same number of projectors may (for example) reasonably be a number such as 18 from a 6 mm diameter sleeve.

In manufacturing other techniques may be used for the alignment of the projectors.

While we have focused on an optimal solution for viewing 3D on a screen, other solutions using the same detectors are possible.

Referring back to FIG. 8, a more conservative approach to creating 3D images is to take an opposite pair of lenses, such as 65 and 66, and having gone through all the alignment procedures above, combine their images as emerging from the processor 101 onto a 3D screen such as one made by Alioscopy (glasses-free), LG (using passive glasses) or Samsung (using active glasses).

Again in FIG. 8 if the surgeon is not satisfied with this point of view he can switch to alternate opposite images as created by lenses 67 and 68, or even by adjacent lenses 65 and 67. This will give the surgeon an orthogonal view, a view at 45°, or other views depending on the total number of lenses and detectors available.

The images created by such opposing detectors will be in 3D. However full parallax, panoramic, glasses-free 3D is probably better obtained using multiple projectors and the Fresnel lens system as described above.

Referring back to FIG. 12 the output from the processor 101 can be programmed to be compressed for transmission according to the protocols of H.264 and MPEG4 AVC, and sent over the Internet or to storage. This is described elsewhere.

While this invention has been described as one in which compact instruments are enveloped by illuminating and sensing sources to create a full panoramic view of an area of operation on the human body, and in which the compact tools can be remotely controlled, in fact to those skilled in the art, the techniques of this invention can be understood and used as means for creating and perfecting tools for many other disciplines, especially those which demand tools for operating in and visualizing in compact spaces. The techniques of this invention may be employed with other materials and in other parts of the electromagnetic spectrum.

It may be understood that although specific terms are employed, they are used in a generic and descriptive sense and must not be construed as limiting. The scope of this invention is set out in the appended claims.

INFORMATION DISCLOSURE

References

1. Adaption and optimization of coding algorithms for mobile 3DTV, Philipp Merckle et al. EU 7$^{th}$ Framework Program
2. SEI Message to indicate stereo video information in progressive H.264 streams Joint Video Team of ISO/IEC MPEG & ITU-T VCEG. Redmond, Wash. July 2004 Henrik Karppinen, Nokia and Shijun Sun, Sharp
3. MainConcept, Reference 2.1 MVC Beta 2, September 2011 "The Reference MVC transcoder includes presets to generate Blu-ray 3D compliant streams that can be played back by any Blu-ray Player and TV supporting 3D content playback. The MainConcept Blu-ray 3D/MVC Encoder is based on the current H.264/AVC Encoder implementation, and includes all of its features. Up to 10 layers are supported, i.e. the different views are encoded as different layers to provide a 3D depth impression of the current picture. In this standard, the encoder receives "N" temporally synchronized video streams and generates one bitstream out of them, i.e. two separate views are coded together. For 3D encoding, it generates one layer for the left and one for right eye."
4. N. Paragios, "Handbook of Mathematical Models in Computer Vision" pages 273-292
5. Robert Szeliski, "Computer Vision" Springer-Verlag 2011 References pp 691-792
6. Photonic Crystals: Molding the Flow of Light, Princeton 2008, Joannopoulos et al.
7. J. Canny, "A Computational Approach to Edge Detection," IEEE Transactions on Pattern Analysis and Machine Intelligence, Vol. PAMI-8, No. 6, 1986, pp. 679-698).

I claim:

1. An instrument for visual examination of and operation on internal body organ(s) through an ear, a nose or a throat, said instrument comprising:
   a jacket with a hollow interior, said jacket defining an operating end and a longitudinally opposite control end of said instrument;
   an outer tube disposed stationary inside said jacket;
   one or more first blades connected rigidly to said outer tube and extending outwardly from said operating end of said instrument;
   an inner tube with a hollow interior, said inner tube disposed for a rotation inside said outer tube during use of said instrument;
   one or more second blades connected rigidly to said inner tube and extending outwardly from said operating end of said instrument, each of said one or more second blades positioned adjacent a respective first blade;
   first fiber optic bundles disposed within a wall thickness of said jacket, said fiber optic bundles are radially spaced from each other about a periphery of said jacket, each fiber optic bundle with a pair of polished ends;
   diffusers, each diffuser being attached, at said control end of said jacket, to one of said polished ends of said each first fiber bundle;
   lenses disposed at said operating end of said instrument, each lens is being attached to a selective first fiber optic bundle from said fiber optic bundles;
   second fiber optic bundles disposed within said wall thickness of said jacket, said second fiber optic bundles interspersed with said first fiber optic bundles; and
   a mechanism positioned at said control end and coupled to said one or more first blades and said one or more second blades.

2. The instrument of claim 1, further comprising detector arrays at said control end of said jacket, said detector arrays configured to collect images from said first fiber optic bundles through said diffusers, from said lenses at said operating end of said jacket.

3. The instrument of claim 1, further comprising light emitting diode (LED) at said control end, said LED configured to illuminate an area at said operating end of said jacket through said second fiber optic bundles.

4. The instrument of claim 3, further comprising detector arrays at said control end of said jacket, said detector arrays configured to collect images from said first fiber optic bundles through said diffusers, from said lenses at said operating end of said jacket.

5. The instrument of claim 4, further comprising projectors, each associated with one detector array, for projecting said images onto a screen for multi-perspective observation in 3D.

6. The instrument of claim 5, further comprising a translucent diffuser screen with a Fresnel lens having a focal length sufficient to separate said images for left and right eye visualization for creating images as stand-alone 3D objects.

7. The instrument of claim 1, wherein each of said jacket, said first tube and said second tube is a flexible member.

8. The instrument of claim 1, wherein said mechanism comprises a pair of handles in a pivotal connection with each other, one of said pair of handles connected to said first tube and another one of said pair of handles connected to said second tube.

9. The instrument of claim 1, further comprising four or more control wires disposed within said wall thickness of said jacket and extending outwardly from said control end, and a toggle arrangement for manipulating said four or more control wires, said toggle arrangement comprising a trackball disposed in a seat being connected to said four or more control wires, a plate, a pivot connected to said trackball with a first portion, a spring disposed about said first portion and being caged between a surface of said plate and a surface of said trackball, and a knob coupled to said pivot with a second portion, where said trackball, said pivot and said knob configured so that when an operator presses said knob left or right or up or down, said operating end of said instrument correspondingly moves in a corresponding direction.

10. The instrument of claim 1, wherein said one or more first blades and said one or more second blades are angled inwards.

11. An instrument for visual examination of, and operation on, internal body organs through natural apertures such as an ear, a nose or a throat, said instrument comprising:
    a jacket with a hollow interior, with a wall thickness sufficient to carry control wires, illumination optics and imaging optics, said jacket defining an operating end and a longitudinally opposite control end of said instrument;
    an outer tube disposed stationary inside said jacket;
    one or more first blades connected rigidly to said outer tube and extending outwardly from said operating end of said instrument;
    an inner tube with a hollow interior, said inner tube disposed for a rotation inside said outer tube;
    one or more second blades connected rigidly to said inner tube and extending outwardly from said operating end of said instrument, each of said one or more second blades positioned to cross with a respective first blade as scissors;

a mechanism at said control end of said instrument, said mechanism for bringing said one or more first blades and said one or more second blades together in a rotary arrangement to function as scissor(s) at said operating end;

first fiber optic bundles disposed within a wall thickness of said jacket, said first fiber optic bundles being spaced from each other on a circumference, each said first fiber bundle having two polished ends, one at said operating end and one at said control end of said jacket;

lenses disposed within said wall thickness of said jacket at said operating end of said instrument, each lens aligned with a respective first fiber optic bundle to image onto one of said polished ends at said operating end;

diffusers, each diffuser being attached to one of said polished ends of each first fiber bundle at said control end of said jacket;

second fiber optic bundles disposed within said wall thickness of said jacket, said second fiber optic bundles interspersed with said first fiber optic bundles;

light emitting diode (LED) at said control end, said LED configured to illuminate an area at said operating end of said jacket through said second fiber optic bundles;

detector arrays at said control end of said jacket, said detector arrays configured to collect images from said first fiber optic bundles through said diffusers, from said lenses at said operating end of said jacket;

projectors, each associated with one detector array, for projecting said images onto a screen for multi-perspective observation in 3D; and a translucent diffuser screen with a Fresnel lens having a focal length sufficient to separate said images for left and right eye visualization for creating images as stand-alone 3D objects.

12. The instrument of claim 11, wherein each fiber bundle is configured to carry binary information which can be sensed on a $Y'C_BC_R$ scale of intensity and color by each appropriate pixel on said detectors.

13. The instrument of claim 11, wherein each first bundle comprises 2μ fibers in a coherent array of a 1 mm total diameter with approximately 200,000 fibers, each fiber imaging on a single 2μ detector element.

14. The instrument of claim 11, wherein each of said jacket, said first tube and said second tube is a flexible member.

15. The instrument of claim 11, comprising four or more control wires disposed within said wall thickness of said jacket and extending outwardly from said control end, and a toggle arrangement for manipulating said four or more control wires, said toggle arrangement comprising a trackball disposed in a seat being connected to said four or more control wires, a plate, a pivot connected to said trackball with a first portion, a spring disposed about said first portion and being caged between a surface of said plate and a surface of said trackball, and a knob coupled to said pivot with a second portion, where said trackball, said pivot and said knob configured so that when an operator presses said knob left or right or up or down, said operating end of said instrument correspondingly moves in a corresponding direction.

16. The instrument of claim 11, wherein said one or more first blades and said one or more second blades are angled inwards.

17. The instrument of claim 11, wherein said mechanism comprises a pair of handles at said control end of said instrument, one handle from said pair of handles connected to said outer tube and another handle from said pair of handles connected to said inner tube, said pair of handles being disposed in a pivotal connection with each other.

18. An instrument for visual examination of and operation on internal body organ(s) through an ear, a nose or a throat, said instrument comprising:

a jacket with a hollow interior, said jacket defining an operating end and a longitudinally opposite control end of said instrument;

an outer tube disposed stationary inside said jacket;

one or more first blades connected rigidly to said outer tube and extending outwardly from said operating end of said instrument;

an inner tube with a hollow interior, said inner tube disposed for a rotation inside said outer tube during use of said instrument;

one or more second blades connected rigidly to said inner tube and extending outwardly from said operating end of said instrument, each of said one or more second blades positioned adjacent a respective first blade;

first fiber optic bundles disposed within a wall thickness of said jacket, said fiber optic bundles are radially spaced from each other about a periphery of said jacket, each fiber optic bundle with a pair of polished ends;

lenses disposed at said operating end of said instrument, each lens is being attached to a selective first fiber optic bundle from said fiber optic bundles;

second fiber optic bundles disposed within said wall thickness of said jacket, said second fiber optic bundles interspersed with said first fiber optic bundles;

light emitting diode (LED) at said control end, said LED configured to illuminate an area at said operating end of said jacket through said second fiber optic bundles;

detector arrays at said control end of said jacket, said detector arrays configured to collect images from said first fiber optic bundles through diffusers, from said lenses at said operating end of said jacket; and a pair of handles disposed at said control end in a pivotal connection with each other, one of said pair of handles connected to said outer tube and another one of said pair of handles connected to said inner tube.

19. The instrument of claim 18, further comprising said diffusers, each diffuser being attached to one of said polished ends of each first fiber bundle at said control end of said jacket.

* * * * *